United States Patent [19]

Greenberg

[11] Patent Number: 5,378,131

[45] Date of Patent: Jan. 3, 1995

[54] CHEWING GUM WITH DENTAL HEALTH BENEFITS EMPLOYING CALCIUM GLYCEROPHOSPHATE

[75] Inventor: Michael J. Greenberg, Northbrook, Ill.

[73] Assignee: The Wm. Wrigley Jr. Company, Chicago, Ill.

[21] Appl. No.: 19,230

[22] Filed: Feb. 18, 1993

[51] Int. Cl.$^6$ .................... A61K 9/68; A61K 33/06
[52] U.S. Cl. ..................... 424/440; 424/48; 424/682; 426/3
[58] Field of Search ................... 424/440, 48

[56] References Cited

U.S. PATENT DOCUMENTS

| | | | |
|---|---|---|---|
| 4,193,988 | 3/1980 | Forward et al. | 424/52 |
| 4,568,537 | 2/1986 | Hoerman et al. | 424/48 |
| 4,767,614 | 8/1988 | Scarpa et al. | 424/48 |
| 4,867,989 | 9/1989 | Silva et al. | 426/5 |
| 4,906,455 | 3/1990 | Hoerman | 424/48 |

OTHER PUBLICATIONS

Featherstone, "An Updated Understanding of the Mechanism of Dental Decay and its Prevention", Nutrition Quarterly, vol. 14, No. 1, 1990, pp. 5–11.
Regolati et al., "Cariostatic Effect of Glycerophosphate", Helv. Odont. Acta, vol. 16, Apr. 1972, pp. 13–18.
Bowen, "The Cariostatic Effect of Calcium Glycerophosphate in Monkeys", Caries Res. 6, pp. 43–51.
Brook, "Calcium Glycerophosphate and Dental Plaque", Caries Res. 9, pp. 156–162 (1975).
Grenby et al., "Protection Against Dental Caries in Rats by Glycerophosphates or Calcium Salts or Mixtures of Both", Archs Oral Biol., vol. 20, No. 11, Nov. 1975, pp. 717–724.
Pianotti et al., "Cariostatic Activity of Calcium Glycerophosphate in Hamsters: Topical vs Dietary Administration", J Dent Res, vol. 55, No. 6, Nov.–Dec. 1976, pp. 1092–1096.

Primary Examiner—Thurman K. Page
Assistant Examiner—James M. Spear
Attorney, Agent, or Firm—Hill, Steadman & Simpson

[57] ABSTRACT

A method and composition for preventing, or reducing the risk of, dental caries. Pursuant to the present invention, a chewing gum is provided that includes a therapeutically effective amount of calcium glycerophosphate. The chewing gum, by including a therapeutically effective amount of calcium glycerophosphate, not only eliminates any cariogenic effects of the chewing gum itself, but actually improves dental health when chewed before or after a meal containing fermentable carbohydrates.

10 Claims, 2 Drawing Sheets

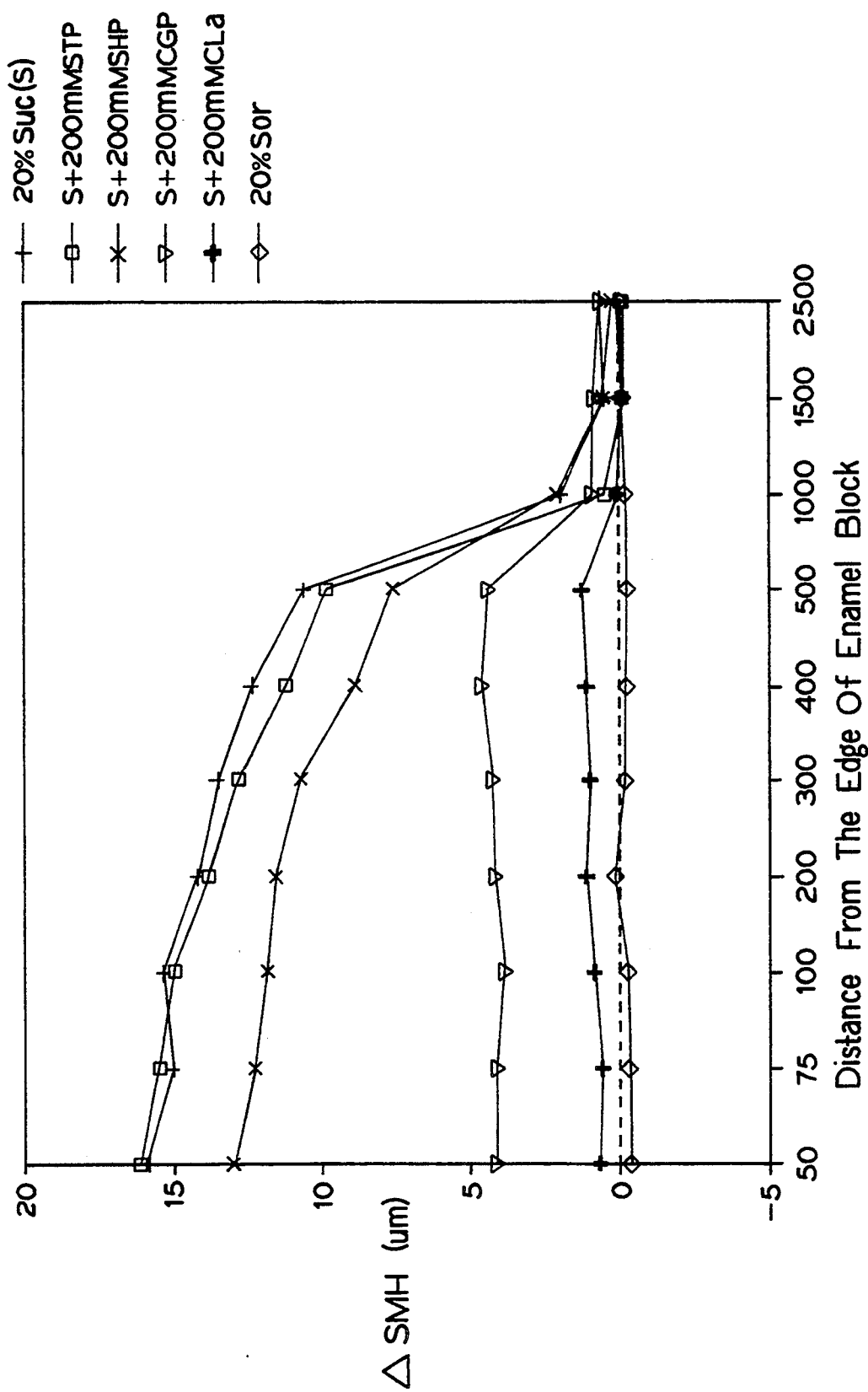

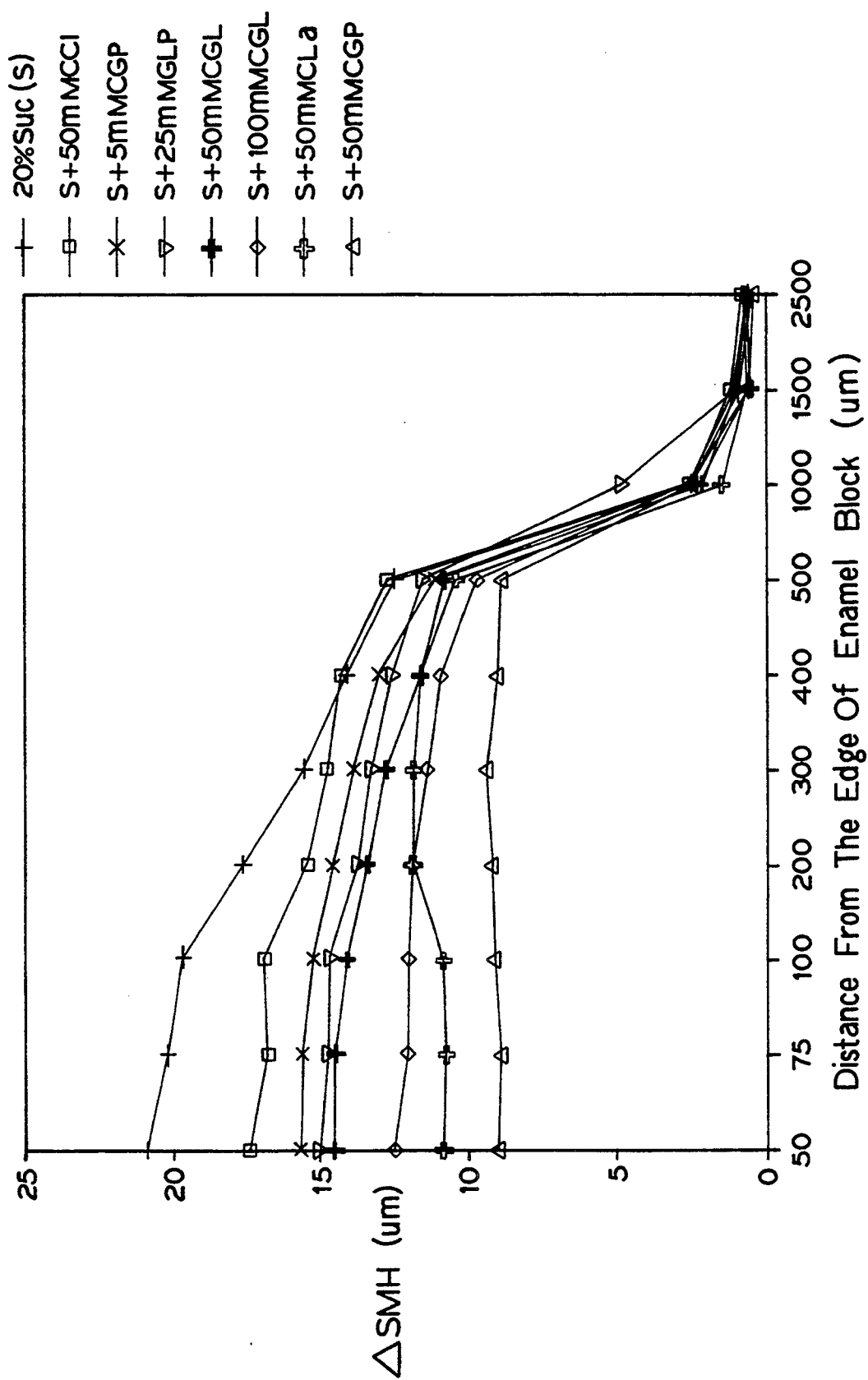

CHEWING GUM WITH DENTAL HEALTH BENEFITS EMPLOYING CALCIUM GLYCEROPHOSPHATE

BACKGROUND OF THE INVENTION

The present invention relates generally to chewing gums. More specifically, the present invention relates to chewing gums that can provide dental benefits.

Except for the common cold, dental caries (tooth decay) is the most prevalent human disorder. See, *The Merck Manual*, Sixteenth Edition, p. 2480. Even though, many steps have been taken to reduce dental caries and tooth decay, such as fluoridation and improved dental care, tooth decay continues to be a significant problem, this is especially true in the adult population; 80% of the tooth decay occurs in 20% of the population. See, Featherstone, *An Updated Understanding of the Mechanism of Dental Decay and its Prevention*, Nutrition Quarterly, Vol. 14, No. 1, 1990, pp. 5–11.

To protect a normal tooth, a thin layer of dental enamel forms a protective coating over the tooth. This coating consists mainly of calcium, phosphate, and other ions in a hydroxyapatite-like structure. The enamel contains 2–5 percent carbonate; this carbonate content makes the enamel susceptible to acid dissolution. See, *Featherstone*, id. at 6.

The interaction of three factors is believed to result in dental caries: a susceptible tooth surface; the proper microflora; and suitable substrate for the microflora. Although several acidogenic micro-organisms that are present in the mouth can initiate carious lesions, *Streptococcus mutans* is believed to be the primary pathogen. See, *The Merck Manual*, supra.

It is know that foods containing fermentable carbohydrates can promote dental caries. Tooth decay begins when the *Streptococcus mutans*, that reside principally in the plaque that adheres to a tooth surface, metabolize the fermentable carbohydrates consumed by the host. During the metabolism of the fermentable carbohydrates by the bacteria, lactic acid and other organic acids are secreted as a by-product. These acids reduce the pH of the surrounding plaque/tooth environment.

When the pH of the plaque/tooth environment drops below a critical level of 5.5 to 5.7, hydroxyapatite (calcium phosphate hydroxide, $Ca_{10}(PO_4)_6(OH)_2$), the key component of tooth enamel, begins to dissolve. Typically, the dissolution begins below the tooth's porous surface.

With repeated acid attacks, caused by the further metabolism of fermentable carbohydrates by the bacteria, subsurface lesions expand. The body's natural remineralization mechanism, however, at this point, can still reverse the decay process. But, if the lesions expand to the point that the enamel surface breaks, a cavity is formed and the process is no longer reversible.

The natural remineralization process involves, in part, the flow of saliva over the plaque. The saliva can raise the pH of the environment. Additionally, calcium and phosphate ions in the saliva precipitate out to replace the hydroxyapatite that was dissolved by the organic acids created during the metabolism of the fermentable carbohydrates.

However, typically, this remineralization process only occurs at significant levels when the pH is above the critical level. Therefore, if the saliva does not sufficiently raise the pH, significant remineralization will not occur. But, the remineralization process may be enhanced by fluoride in the oral cavity that speeds up new crystal growth and makes a fluorapatite-like material that is precipitated on the surface of the crystals inside the carie lesion. See, *Featherstone, id.* at 7.

Although a number of salts have been reported in certain experiments to counteract the decay process, no acceptable method of treatment using such salts, in the opinion of the inventor of the present invention, has been provided. One of the difficulties is providing a viable vehicle for delivering the salts. Still further, a number of safety issues are raised by some of the salts. Furthermore, sensory problems with respect to some of the salts prevent these salts from being taken on a regular basis by a patient to provide prophylactic benefits.

SUMMARY OF THE INVENTION

The present invention provides a composition and method for preventing, or reducing the risk of, dental caries. Pursuant to the present invention, a chewing gum is provided that includes a therapeutically effective amount of calcium glycerophosphate.

Calcium glycerophosphate counteracts the decay process. It is believed to function by reducing demineralization and/or increasing remineralization of tooth enamel. Calcium glycerophosphate may also provide a buffering effect to prevent low pHs from occurring in the plaque. Still further, calcium glycerophosphate may interfere with *Streptococcus mutans*' metabolic process and thus prevent or reduce formation of lactic acid.

Calcium glycerophosphate has been found to be the only effective enamel remineralizing agent which is acceptable from sensory and safety standpoints. Accordingly, calcium glycerophosphate can be used in chewing gum. Chewing gum is an especially good vehicle for delivering calcium glycerophosphate because it can deliver the ingredient over prolonged periods of time and can be conveniently used almost anywhere at anytime as opposed to a rinse or dentifrices.

To this end, a method for preventing dental caries is provided comprising the step of chewing a gum that includes a therapeutically effective amount of calcium glycerophosphate before, during, or after the ingestion of fermentable carbohydrates.

The present invention also provides a method for reducing the cariogenic properties of a sugar containing gum. The method includes the step of adding to a sugar containing gum a sufficient amount of calcium glycerophosphate to offset the cariogenicity of the sugar present in the gum.

Further, the present invention provides a chewing gum for reducing the generation of dental caries comprising: a water insoluble base; a water soluble portion and flavor; and at least 0.5% by weight calcium glycerophosphate.

In an embodiment, the chewing gum is substantially wax free.

In an embodiment, the chewing gum is a low moisture gum, e.g., a gum containing less than 2% by weight water.

In an embodiment, the chewing gum is a low calorie chewing gum.

In an embodiment, the chewing gum contains other therapeutic agents, other than fluoride, for preventing dental caries.

In an embodiment, the calcium glycerophosphate includes both the α and β isomers.

The present invention also provides a sugar containing gum that does not have cariogenic properties comprising: a water insoluble base; a water soluble portion that includes sugar; and a sufficient amount of calcium glycerophosphate to offset the cariogenic properties of the sugar.

An advantage of the present invention is to provide a method for preventing, or reducing the risk of, dental caries.

Additionally, an advantage of the present invention is to provide a chewing gum that can be used to improve dental health.

Further, an advantage of the present invention is to provide a sugar containing chewing gum that does not have cariogenic properties.

Furthermore, an advantage of the present invention is to provide a chewing gum, that does not have the sensory draw backs of a sugarless chewing gum, but does not promote dental caries.

Moreover, an advantage of the present invention is to provide an easy and enjoyable way to improve dental health.

Still further, an advantage of the present invention is to provide a composition and method for delivering a therapeutic agent over a prolonged period of time to the oral region.

Additional features and advantages of the present invention are described in, and will be apparent from, the detailed description of the presently preferred embodiments and from the drawings.

BRIEF DESCRIPTION OF THE DRAWINGS

FIG. 1 illustrates, graphically, results from experiments performed in Example 1 relating to changes in hardness of test enamel.

FIG. 2 illustrates, graphically, results from experiments performed in Example 2 relating to changes in hardness of test enamel.

DETAILED DESCRIPTION OF THE PRESENTLY PREFERRED EMBODIMENTS

The present invention provides a method and composition for preventing, or reducing the risk of, dental caries. Pursuant to the present invention, a chewing gum is provided that includes a therapeutically effective amount of calcium glycerophosphate. The chewing gum of the present invention, by including a therapeutically effective amount of calcium glycerophosphate, not only eliminates any cariogenic effects of the chewing gum itself, but actually improves dental health when chewed before or after a meal containing fermentable carbohydrates.

Calcium glycerophosphate is believed to function by reducing demineralization and/or increasing remineralization of tooth enamel. As calcium glycerophosphate diffuses into the plaque, it raises the concentration of calcium and phosphate ions in the plaque. At low pHs, the increased concentration of calcium and phosphate ions suppresses dissolution of enamel. This is due to the fact that these ions drive the dissociation equation toward undissociated hydroxyapatite.

Calcium glycerophosphate also provides a source of calcium and phosphate ions that promotes remineralization of enamel that has been damaged by acid. In contrast to the body's natural remineralization process, this remineralization process can proceed even at low pHs of 5 to 7. A further advantage of calcium glycerophosphate is it may also bind directly to the enamel surface.

Still further, calcium glycerophosphate may also provide a buffering effect. This will prevent low pHs from occurring in the plaque. Still further, calcium glycerophosphate may interfere with the metabolic process of *Streptococcus mutans*. This may prevent or reduce the initial formation of organic acids, such as lactic acid.

Pursuant to the present invention, calcium glycerophosphate is incorporated into chewing gum. The chewing gum may be any of a variety of different chewing gums including low or high moisture, sugar or sugarless, wax-containing or wax-free, low calorie (via high base or low calorie bulking agents), and/or may contain other dental health agents.

Chewing gum generally consists of a water insoluble gum base, a water soluble portion, and flavors. The water soluble portion dissipates with a portion of the flavor over a period of time during chewing. The gum base portion is retained in the mouth throughout the chew.

The insoluble gum base generally comprises elastomers, resins, fats and oils, softeners, and inorganic fillers. The gum base may or may not include wax. The insoluble gum base can constitute approximately 5 to about 95 percent, by weight, of the chewing gum, more commonly, the gum base comprises 10 to about 50 percent of the gum, and in some preferred embodiments, 20 to about 35 percent, by weight, of the chewing gum.

In an embodiment, the chewing gum base of the present invention contains about 20 to about 60 weight percent synthetic elastomer, 0 to about 30 weight percent natural elastomer, about 5 to about 55 weight percent elastomer plasticizer, about 4 to about 35 weight percent filler, about 5 to about 35 weight percent softener, and optional minor amounts (about one percent or less) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5 to about 50 percent by weight of the copolymer, and combinations thereof.

Preferred ranges are, for polyisobutylene, 50,000 to 80,000 GPC weight average molecular weight, for styrene-butadiene, 1:1 to 1:3 bound styrene-butadiene, for polyvinyl acetate, 10,000 to 65,000 GPC weight average molecular weight with the higher molecular weight polyvinyl acetates typically used in bubble gum base, and for vinyl acetate-vinyl laurate, vinyl laurate content of 10–45 percent.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is abhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters of partially hydrogenated rosin, glycerol esters polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof.

Colorants and whiteners may include FD&C-type dyes and lakes, fruit and vegetable extracts, titanium dioxide, and combinations thereof.

The base may or may not include wax. An example of a wax-free gum base is disclosed in U.S. Ser. No. 07/906,921, U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5 to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute 5 to about 95% by weight of the chewing gum, more typically, 20 to 80% by weight, and more commonly, 30 to 60% by weight of the gum.

Sugar sweeteners generally include saccharide-containing components commonly known in the chewing gum art, including, but not limited to, sucrose, dextrose, maltose, dextrin, dried invert sugar, fructose, levulose, galactose, corn syrup solids, and the like, alone or in combination.

Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination with the above. Preferred sweeteners include, but are not limited to sucralose, aspartame, salts of acesulfame, alitame, saccharin and its salts, cyclamic acid and its salts, glycyrrhizin, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Usage level of the artificial sweetener will vary greatly and will depend on such factors as potency of the sweetener, rate of release, desired sweetness of the product, level and type of flavor used and cost considerations. Thus, the active level of artificial sweetener may vary from 0.02 to about 8%. When carriers used for encapsulation are included, the usage level of the encapsulated sweetener will be proportionately higher.

Combinations of sugar and/or sugarless sweeteners may be used in chewing gum. Additionally, the softener may also provide additional sweetness such as with aqueous sugar or alditol solutions.

If a low caloric gum is desired, a low caloric bulking agent can be used. Example of low caloric bulking agents include: polydextrose; Raftilose Raftilin;Fructooligosaccharides (NutraFlora);Palatinose oligosaccharide; Guar Gum Hydrolysate (Sun Fiber); or indigestible dextrin (Fibersol). However, other low calorie bulking agents can be used.

A variety of flavoring agents can be used. The flavor can be used in amounts of approximately 0.1 to about 15 weight percent of the gum, and preferably, 0.2 to 5%. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

Pursuant to the present invention, calcium glycerophosphate is added to the chewing gum composition. In an embodiment, at least 0.5% calcium glycerophosphate, by weight, is used in the chewing gum. At least at this level, it is believed that a therapeutically effective amount of calcium glycerophosphate is provided; although reduced levels may still provide dental benefits. In a preferred embodiment, calcium glycerophosphate is provided at a level of between approximately 1.0 to about 7.0% of the total weight of the chewing gum. In a most preferred embodiment, the chewing gum contains approximately 1.5 to about 4.0 weight percent calcium glycerophosphate.

The chewing gum may either be sugarless or sugar containing. However, in an embodiment of the present invention, the chewing gum is sugar containing. This provides an advantageous chewing gum wherein calcium glycerophosphate offsets any detrimental cariogenic effects of the sugar. The resultant chewing gum is not only non-cariogenic, but, can provide anti-cariogenic properties. This also overcomes some of the sensory quality problems of sugarless gums. Still further, such a chewing gum overcomes some of the other problems of sugarless gum. For example, some sugarless gums may be poorly tolerated by some chewers, who manifest gastrointestinal disturbances, because of the sugar alcohols used in sugarless gums.

There are two structural isomers of calcium glycerophosphate. These are called the α and β isomers. These two structural isomers are illustrated below:

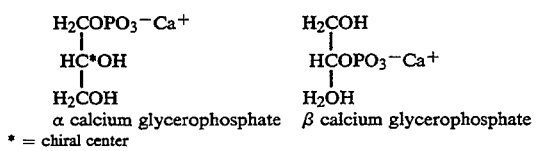

α calcium glycerophosphate    β calcium glycerophosphate

\* = chiral center

In the α isomer, the phosphate radical is attached to the first carbon on the glycerin chain making the second carbon a chiral center. The α form therefore has two optical isomers.

In the β form, the phosphate is attached to the second (middle) carbon which is symmetric (achiral). α is the predominant form.

Although it is uncertain what effect, if any, the physical differences between the isomers have on dental benefits, release rate, or sensory acceptability, it is possible that the benefits can be increased by optimizing the ratio between the two isomers.

By way of example, and not limitation, experiments illustrating the benefits of the present invention will now be given:

EXAMPLE NO. 1

To test the efficacy of certain salts as dental health agents, volunteers were fitted with dental appliances in which blocks of bovine enamel were mounted. Such intra-oral models have been used in the medical and dental arena to demonstrate the efficacy of certain agents, as well as the detrimental dental effects of certain food products. See, Featherstone, id. at 10.

The test enamel was covered with a plaque prepared by cultivating Streptococcus mutans in a nutrient broth. The volunteers then rinsed with a test solution (test solutions are set forth in Table 1) for one minute, followed by a 45 minute incubation period. The enamel blocks were then removed and surface microhardness (SMH) measurements were made on the cross-sectional edge to evaluate demineralization caused by Streptococcus mutans' metabolism of the sugar in the test solutions.

The enamel had been previously tested for hardness before exposure to the solution to provide a baseline hardness which was used to calculate a change in hardness due to the acid attack. The measurements were made at ten distances from the edge of the block (correspondence to depths below the surface of the enamel). The distances (depths) were 50, 75, 100, 200, 300, 400, 500, 1000, 1500, and 2500 microns.

The hardness changes at 300 microns are given in Table 1. The 300 micron ΔSMH values are typical (in terms of relative differences between salts and statistical significance) to values at depths of 500 microns or less. At 1000 microns and deeper, there was essentially no softening of the enamel, presumably because the acid attack had not penetrated that far.

A higher ΔSMH value indicates greater enamel dissolution (softening). Standard deviations (n=5) are also given. Complete results are presented graphically in FIG. 1.

TABLE 1

| Test Solution | ΔSMH (SD) at 300 microns |
|---|---|
| 20% Sucrose (positive control) | 14.36 (3.1) |
| 20% Sucrose + 0.2M Sodium Trimetaphosphate | 11.88 (2.3) |
| 20% Sucrose + 0.2M Sodium Hexametaphosphate | 11.89 (2.0) |
| 20% Sucrose + 0.2M Calcium Glycerophosphate (CaGP) | 3.60 (2.1) |
| 20% Sucrose + 0.2M Calcium Lactate | 1.27 (0.9) |
| 20% Sorbitol (negative control) | −0.18 (0.5) |

Statistical analysis determined that, at a 95% confidence level, there was no significant difference between the two calcium salts, but the difference between each of them and the sodium salts (and the sucrose control) was significant. The difference between the sorbitol control, calcium lactate and CaGP was not significant.

EXAMPLE NO. 2

The evaluation set forth in Example No. 1 was then repeated with three levels of CaGP, as well as two levels of calcium gluconate, one level of the calcium chloride, and a lower level of the calcium lactate. The ΔSMH results at 300 microns for this second test are given in Table 2. Complete results are illustrated graphically in FIG. 2.

TABLE 2

| Test Solution | ΔSMH (SD) at 300 microns |
|---|---|
| 20% Sucrose (positive control) | 15.6 (2.1) |
| 20% Sucrose + 0.05M Calcium Chloride | 14.8 (1.8) |
| 20% Sucrose + 0.005M CaGP | 13.9 (1.8) |
| 20% Sucrose + 0.025M CaGP | 13.0 (1.7) |
| 20% Sucrose + 0.050M CaGP | 9.5 (3.4) |
| 20% Sucrose + 0.050M Calcium Gluconate | 12.8 (1.3) |
| 20% Sucrose + 0.100M Calcium Gluconate | 11.4 (2.4) |
| 20% Sucrose + 0.050M Lactate | 11.9 (3.0) |

In this test the 0.050M CaGP was significantly better than all other solutions except the 0.100M calcium gluconate and the 0.050 calcium lactate (which were not significantly different). The two lower levels of CaGP were significantly better than the sucrose control (and the calcium chloride solution).

EXAMPLE NO. 3

Chewing gums were then prepared to test the rate of CaGP release during chewing. The following formulas were used:

| | Example 1 (Control) | Example 2 (a and b) 2.5% CaGP |
|---|---|---|
| Sugar | 54.24 | 51.74 |
| Gum Base | 20.68 | 20.68 |
| Corn Syrup | 13.17 | 13.17 |
| Dextrose | 10.15 | 10.15 |
| Glycerin | 1.20 | 1.20 |
| Spearmint Flavor | 0.56 | 0.56 |
| CaGP | — | 2.50 |
| | 100.00 | 100.00 |

The gum of Example 2 was made twice using CaGP from two different sources.

2a: Iwaki Seiyaku Co. Ltd., Tokyo (Distributed by Austin Chemical Company, Rosemont, Ill.)

2b: Givaudan Lavirotte (Distributed by Roussel Corp., Englewood Cliffs, N.J.)

The three gums were chewed by volunteers. Chewed cuds were collected after 1, 2, 5, 10, and 15 minutes of chewing. The cuds were analyzed for residual calcium and phosphorous.

Table 3 gives the percentage of each ion released from examples 2a and 2b. The control sample was used to account for the calcium and a small quantity of phosphorous present in the cuds due to calcium carbonate and other components in the gum base and other ingredients. The analyses showed that essentially none of the calcium or phosphorous normally present in gum is released during a fifteen minute chew.

TABLE 3

| Chew Time | % of original CaGP released (Ca/P) | |
| --- | --- | --- |
|  | Example 2a | Example 2b |
| 0 | 0/0 | 0/0 |
| 2 | 24/24 | 29/39 |
| 5 | 46/50 | 52/56 |
| 10 | 67/69 | 55/66 |
| 15 | 71/77 | 62/72 |

Assuming that saliva flow starts at 5 ml/min. in the early chew and drops to about 1.5 ml/min. after the first two minutes, these release rates would result in CaGP levels in saliva in the 0.006M to 0.010M range during the first ten minutes and lower levels thereafter. As noted above, CaGP levels of 0.005M and higher provide statistically significant benefits. That is, they reduce the cariogenicity of sugar by reducing demineralization and/or promoting remineralization. Since essentially all of the sugar in gum is extracted in the first three to four minutes of chewing, even lower levels of CaGP are likely to provide dental benefits when administered after that time.

EXAMPLE NO. 4

The three examples (1, 2a, and 2b) were evaluated by four expert panelists in an informal, single-blind sensory test. Compared to the control, the two experimental samples were considered borderline acceptable/unacceptable by standards of commercial sugar products. However, the sensory defects attributable to the CaGP (drying mouthfeel, weak flavor) are considered tolerable for a dental health product and may be correctable to a large extent through optimization of base, flavor and other gum ingredients.

It is possible that through careful formulation, even higher levels would be tolerable in a dental health gum. Examples of such formulation steps would include: increased levels of base; selection of masking flavors and/or use of higher flavor levels; and use of higher sweetener levels especially high intensity sweeteners.

In contrast, the other salts which are believed to be effective in preventing demineralization of tooth enamel are intolerable in chewing gum even at low levels. For example, aqueous solutions of 2.5 mg/ml of various salts were tasted by an informal panel of three people. (This level corresponds to a level of approximately 1.25% in gum.) At this level CaGP had little or no taste and only slight astringency. Calcium acetate had a noticeable vinegar taste and calcium lactate had a slight to moderate salty taste and slight mouth coating. Calcium gluconate also had little or no taste. The three most acceptable salts were then tried at 10 mg/ml (corresponding to about 4.8% in gum). Calcium chloride was intensely salty and calcium gluconate had little or no taste but was slightly astringent and burning. Calcium glycerophosphate had no taste but had some mouth coating effect.

As can be seen in Table 4, CaGP was the only salt tested which was both effective and well tolerated sensorially.

TABLE 4

|  | Effectiveness | Sensory |
| --- | --- | --- |
| Na Trimetaphosphate | Poor | NA |
| Na Hexametaphosphate | Poor | NA |
| CaGP | Good | Good |
| Ca Lactate | Good | Poor |
| Ca Chloride | Poor | Fair |
| Ca Gluconate | Fair | Good |

By way of example, and not limitation, contemplative examples of compositions including calcium glycerophosphate of the present invention will now be given:

|  | Example 3 | Example 4 | Example 5 |
| --- | --- | --- | --- |
| Sorbitol | 54.30 | 52.10 | 48.50 |
| Mannitol | 1.00 | 1.00 | 1.00 |
| Lycasin | — | 8.20 | 8.20 |
| Gum Base | 30.00 | 30.00 | 30.00 |
| Peppermint Flavor | 0.90 | 1.20 | 1.40 |
| Glycerin | 12.80 | 4.90 | 6.10 |
| Encapsulated APM | 0.50 | 0.60 | 0.80 |
| CaGP | 0.50 | 2.00 | 4.00 |
|  | 100.00 | 100.00 | 100.00 |

Examples 3-5 illustrate sugarless embodiments

|  | Example 6 | Example 7 | Example 8 |
| --- | --- | --- | --- |
| Sugar | 53.00 | 49.20 | 43.90 |
| Wax-Free Gum Base | 22.00 | 22.00 | 22.00 |
| Corn Syrup | 12.00 | 12.00 | 14.00 |
| Dextrose | 10.00 | 10.00 | 10.00 |
| Glycerin | 1.50 | 1.50 | 1.50 |
| Wintergreen Flavor | 0.80 | 0.90 | 1.00 |
| Encapsulated APM | 0.20 | 0.40 | 0.60 |
| CaGP | 0.50 | 4.00 | 7.00 |
|  | 100.00 | 100.00 | 100.00 |

Examples 6-8 illustrate sugar gums with encapsulated aspartame to mask the astringency of CaGP. They also utilize mineral hydrocarbon wax-free bases.

|  | Example 9 | Example 10 |
| --- | --- | --- |
| Gum Base | 85.22 | 94.16 |
| Glycerin | 10.00 | — |
| Cinnamon Flavor | 3.00 | 3.00 |
| Alitame | 0.03 | 0.04 |
| Encapsulated Sucralose | 0.25 | 0.30 |
| CaGP | 1.50 | 2.50 |
|  | 100.00 | 100.00 |

Examples 9 and 10 illustrate high-base, low calorie gums: low calorie gums could also be produced through the use of low calorie bulking agents such as polydextrose, indigestible dextrin, guar gum hydrolysate, fructooligosaccharide, oligofructose, inulin and palatinose oligosaccharide.

|  | Example 11 |
| --- | --- |
| Gum Base | 25.00 |
| Sugar | 53.10 |
| Corn Syrup | 12.00 |
| Dextrose | 8.00 |

-continued

|  | Example 11 |
| --- | --- |
| Glycerin | 1.00 |
| Peppermint Flavor | 0.90 |
|  | 100.00 |

The gum of Example 11 can be dusted with a rolling compound containing CaGP.

The following examples illustrate CaGP rolling compounds which may be applied to the gum of Example 11.

|  | Example 12 | Example 13 | Example 14 |
| --- | --- | --- | --- |
| CaGP | 90% | 70% | 70% |
| Sugar | — | 20% | — |
| APM | 10% | 10% | 5% |
| Talc | — | — | 25% |
|  | 100.00 | 100.00 | 100.00 |

The rolling compound is applied at a level such that it comprises approximately 2% of the finished, dusted gum. At this level, the gums will contain 1.8% (Example 12) and 1.4% (Examples 13 and 14) CaGP.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A chewing gum for reducing the generation of dental caries, the chewing gum not including fluoride and comprising:
    a water insoluble base portion;
    a water soluble portion;
    a flavor agent; and
    at least 0.5% by weight calcium glycerophosphate incorporated in the water insoluble base portion and water soluble portion.
2. The chewing gum of claim 1 wherein the chewing gum includes sugar.
3. The chewing gum of claim 1 wherein the chewing gum is wax free.
4. The chewing gum of claim 1 wherein the chewing gum is a low calorie chewing gum.
5. The chewing gum of claim 1 wherein the chewing gum contains other therapeutic agents, other than fluoride, for preventing dental caries.
6. The chewing gum of claim 1 wherein the calcium glycerophosphate includes both $\alpha$ and $\beta$ isomers.
7. A sugar containing chewing gum comprising:
    a water insoluble base;
    a water soluble portion including sugar; and
    a sufficient amount of calcium glycerophosphate, that is incorporated in the water insoluble base and water soluble portion to offset the cariogenic properties of the sugar without the need for other therapeutic agents for preventing dental caries.
8. The chewing gum of claim 7 wherein the chewing gum is wax free.
9. The chewing gum of claim 7 wherein the gum is a low calorie chewing gum.
10. The chewing gum of claim 7 wherein the calcium glycerophosphate comprises approximately 0.5% to about 7.0% by weight of the chewing gum.

* * * * *